United States Patent [19]

Chien et al.

[11] 4,032,645

[45] June 28, 1977

[54] INJECTABLE METRONIDAZOLE COMPOSITION

[75] Inventors: Yie W. Chien, Skokie; Dianne M. Jefferson, Chicago, both of Ill.

[73] Assignee: G. D. Searle & Co., Chicago, Ill.

[22] Filed: June 19, 1975

[21] Appl. No.: 588,211

[52] U.S. Cl. .................................................. 424/273
[51] Int. Cl.² .................................... A61K 31/415
[58] Field of Search ................. 424/273; 260/309

[56] References Cited

UNITED STATES PATENTS

| | | | |
|---|---|---|---|
| 2,944,061 | 7/1960 | Jacob et al. | 260/309 |
| 2,980,584 | 4/1961 | Hammer | 424/227 |
| 3,551,554 | 12/1970 | Herschler | 424/273 |

*Primary Examiner*—V. D. Turner
*Attorney, Agent, or Firm*—John J. McDonnell

[57] ABSTRACT

An injectable solution suitable for the systemic treatment of anaerobic infections is prepared by solubilization of 500–650 mg. metronidazole in 10 ml. of a solvent system comprised of:
  25–35% v/v N,N-dimethylacetamide
  40–60% v/v ethanol
  10–30% v/v aqueous buffer
or,
  15–25% v/v N,N-dimethylacetamide
  40–60% v/v ethanol
  10–30% v/v aqueous buffer
and including one of the following:
  1–5% v/v nicotinamide
  5–15% v/v propylene glycol
  5–15% v/v 2,2-dimethyl-1,3-dioxolane-4-methanol,
the aqueous buffer maintaining the pH at 5.0–7.5.

4 Claims, 6 Drawing Figures

INJECTABLE METRONIDAZOLE COMPOSITION

BACKGROUND OF THE INVENTION

In the systemic treatment of anaerobic infections a parenteral mode of administration is advantageous for patients who are seriously ill and for whom oral administration is not feasible or may be considered to be insufficiently incisive. Heretofore, a practical way of administering a parenteral dose of metronidazole was not available since the aqueous solubility of metronidazole is only about 100 mg./10 ml. and a practical dosage is in the 500–650 mg./10 ml. range. Those skilled in the art recognize the practical advantages of a single 10 ml. injectable dosage form as opposed to the large volume of solution which would be needed to administer a 500–650 mg. dose of metronidazole in an aqueous solution. Thus, this invention provides a convenient and practical dosage form for the systemic treatment of anaerobic infections.

Generally, parenteral solutions are preferable for injections since they avoid the disadvantages inherent in suspensions, such as nonuniform dosage, caking, and possible slow release of the medicament when it is not desired. However, when wholly aqueous solvent systems are unsuitable, the choice of a nonaqueous system requires consideration of numerous parameters. The chosen solvent system must be nontoxic, nonirritating, and nonsensitizing. It also must exert no pharmacologic activity of its own, nor adversely affect the action of the drug. Additionally, the system must be stable under normal conditions of pharmaceutical use and not adversely affect the stability of the drug. The viscosity must be such as to allow for ease of injection, and the solvent must remain fluid over a fairly wide temperature range. Other considerations are water and body fluid miscibility, the degree of flammability, availability, source of supply and constant purity.

SUMMARY OF THE INVENTION

The present invention is concerned with an injectable solution suitable for the systemic treatment of anaerobic infections. More particularly, such an injectable solution is prepared by solubilization of 500–650 mg. metronidazole in 10 ml. of a solvent system comprised of
15–35% v/v N,N-dimethylacetamide
40–60% v/v ethanol
10–30% v/v aqueous buffer
which may include one of the following:
1–5% w/v nicotinamide
5–15% v/v propylene glycol
5–15% v/v 2,2-dimethyl-1,3-dioxolane-4-methanol
the aqueous buffer maintaining the pH at 5.0–7.5, preferably 5.0–6.0.

DETAILED DESCRIPTION OF THE INVENTION

Figure 1:
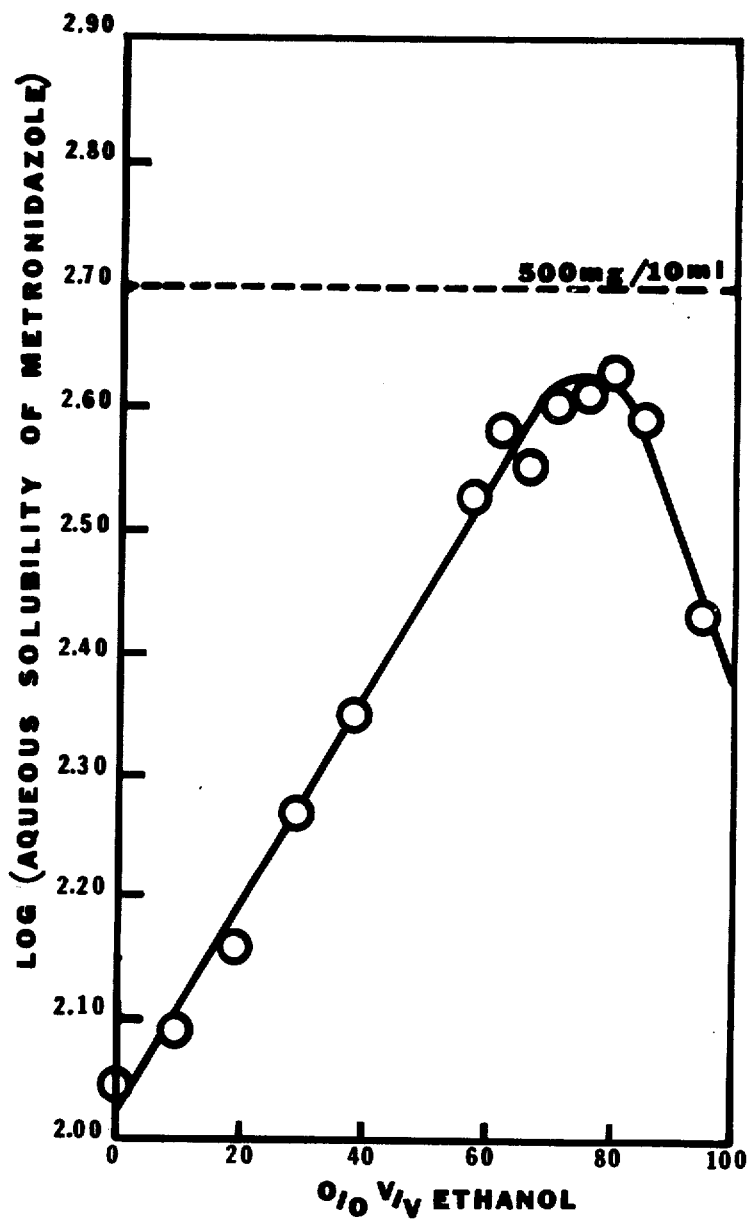
FIG. 1 is a graph illustrating the solubility of metronidazole in various mixtures of water and ethanol.

According to the present invention, it has now been found that the required concentration of 500–650 mg./10 ml. of metronidazole can be attained by utilizing a solvent system having the above properties. Thus, a solvent system suitable for an injectable solution containing 500–650 mg./10 ml. of metronidazole is comprised of:
25–35% v/v N,N-dimethylacetamide
40–60% v/v ethanol
10–30% v/v aqueous buffer
or
15–25% v/v N,N-dimethylacetamide
40–60% v/v ethanol
10–30% v/v aqueous buffer
and including one of the following:
1–5% w/v hydrotropic agent
5–15% v/v polyhydroxyl alcohol
5–15% v/v dioxolane derivative
said aqueous buffer maintaining the pH at 5.0–7.5.

As metronidazole is most stable at a pH range of 5.0–7.5, stability and shelf life are enhanced by using an appropriate aqueous buffer. Any non-toxic, pharmaceutically acceptable, aqueous buffer capable of buffering in the pH 5.0–7.5 range is operable in this invention. A particularly preferred aqueous buffer is Tris(hydroxymethyl)aminomethane buffer [Tris] such as that available from Sigma Chemical Co., St Louis, Mo., marketed under the trademark Trizma.

Desirable polyhydroxyl alcohols include, but are not limited to, propylene glycol (1,2-propanediol), and 1,3-butylene glycol (1,3-butanediol).

The term "hydrotropic agent" refers to an agent which forms a solubility-increasing complex. Hydrotropic agents which are useful in the present invention include, but are not limited to, nicotinamide (niacin), ascorbic acid, 3-pyridylcarbinol and 4-pyridylcarbinol. A particularly preferred hydrotropic agent is nicotinamide.

Typical dioxolanes contemplated for use in this invention include 2,2-dimethyl-1,3-dioxolane-4-methanol (Solketal, isopropylidene glycerol, glycerol dimethylketal) and glycerol formal (25:75 3-hydroxymethyl-1,3-dioxolane: 5-hydroxydioxane).

The addition of a polyhydroxyl alcohol, hydrotropic agent and/or a dioxolane has the advantage of enabling one to decrease the dialkylacetamide percentage in the solvent system, while still retaining ability to dissolve the 500–650 mg./10 ml. concentration of metronidazole. This decreased percentage of the dialkylacetamides is particularly advantageous since these solvents exhibit undesirable side effects in high doses, e.g., liver damage and hallucinations. See, for instance, Horn, Toxicol. Appl. Pharmacol., 3,12 (1961) and Weiss et.

al., *Science*, 136, 751 (1962). While concentrations of N,N-dimethylacetamide of 50% or less are widely used in formulations, [see, for instance, U.S. Pat. Nos. 2,980,584 and 2,990,333, and British Pat. No. 886,996] any minimization of concentration is advantageous.

Thus, a particularly preferred solvent system for dissolving 500–650 mg./10 ml. of metronidazole comprises:

15–25% v/v N,N-dimethylacetamide
40–60% v/v ethanol
10–30% v/v aqueous buffer and includes one of the following:

1–5% w/v nicotinamide
5–15% v/v propylene glycol
5–15% v/v 2,2-dimethyl-1,3-dioxolane-4-methanol said aqueous buffer maintaining the pH of 5.0–7.5.

The critical features of the solubility of metronidazole, [1-(2-hydroxyethyl)-2-methyl-5-nitroimidazole] are evident from FIGS. 1 through 6.

FIG. 1 indicates that 100% water, 100% ethanol and all mixtures of water and ethanol do not dissolve a suitable amount of metronidazole. It is observed that the optimum solubility in water-ethanol mixtures occur at about 80% ethanol. Due to the solubility of metronidazole in both 100% water and in 100% ethanol, one skilled in formulation arts would be led away from using these solvents as major components in a solvent system.

Figure 2:
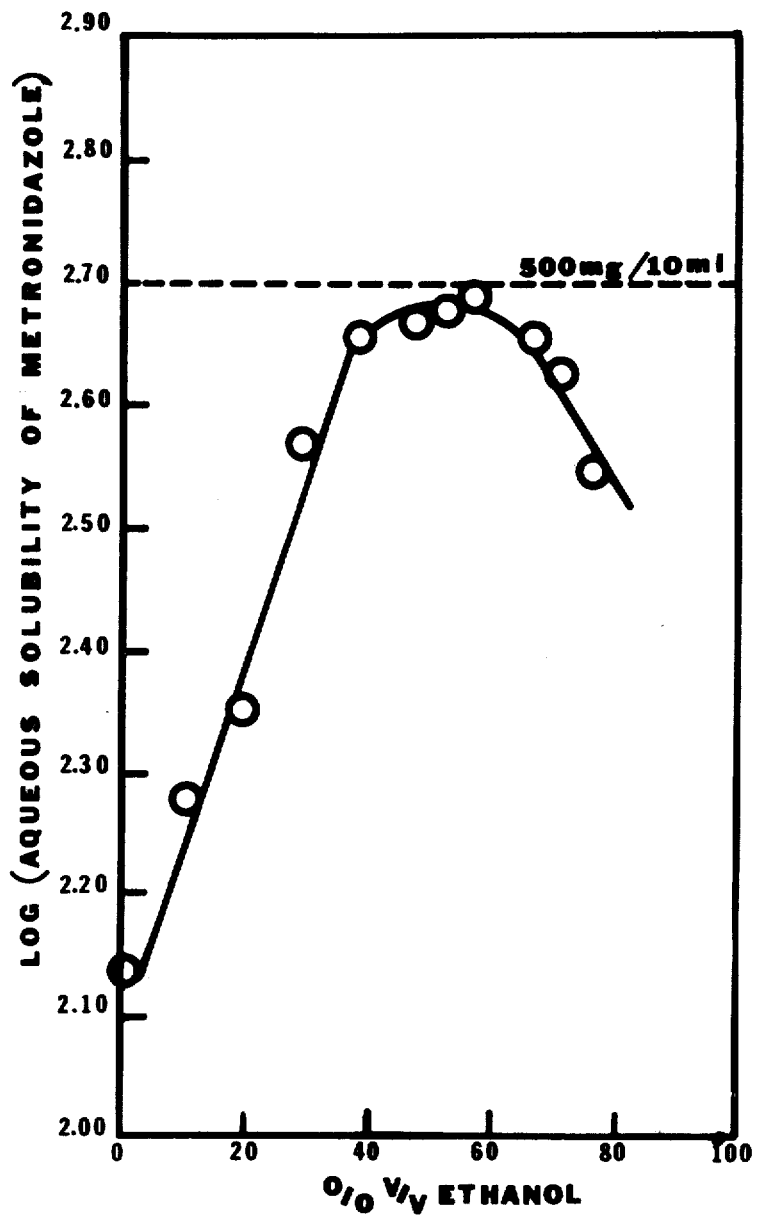
FIG. 2 is a graph illustrating the solubility of metronidazole in various mixtures of water and ethanol with a constant composition of 20% v/v N,N-dimethylacetamide.

It is considered desirable to maintain N,N-dimethylacetamide concentrations in any formulation at a relatively low level. In FIG. 2, it is shown that 20% N,N-dimethylacetamide is not a suitable solvent system in combination with water or ethanol alone. Those satisfied with less desirable formulation could use a solvent system of 20% N,N-dimethylacetamide, 40% water, and 40% ethanol. But as before, the low solubility of metronidazole in 20% N,N-dimethylacetamide-water alone or 20% N,N-dimethylacetamide-ethanol alone would lead one skilled in the art to abandon a combination of water-ethanol and 20% N,N-diemthylacetamide. One would also believe this for combinations of 30% N,N-dimethylacetamide and water and ethanol.

Figure 3:
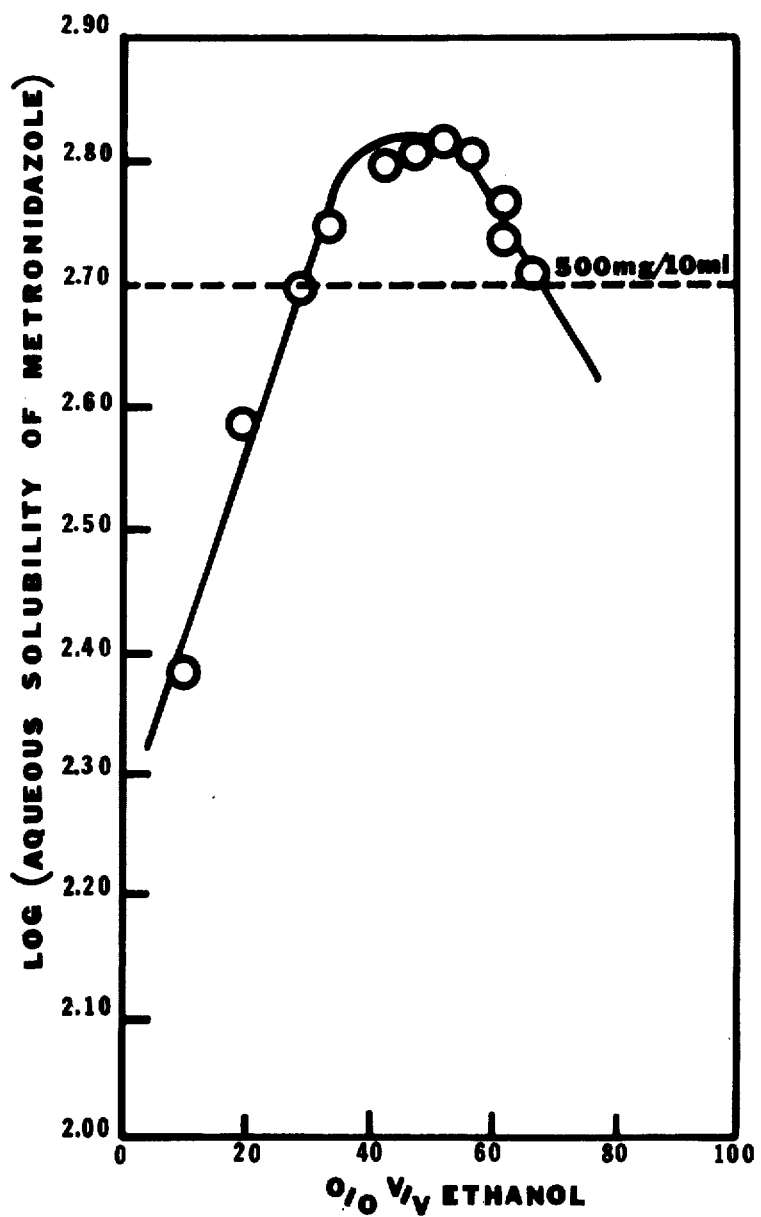
FIG. 3 is a graph illustrating the solubility of metronidazole in various mixtures of water and ethanol with a constant composition of 30% v/v N,N-dimethylacetamide.

It can be observed from FIG. 3 that, unexpectedly, a solvent system of 30% N,N-dimethylacetamide in combination with the indicated proportions of ethanol and water solubilizes more than 500 mg./10 ml. of metronidazole.

Figure 4:
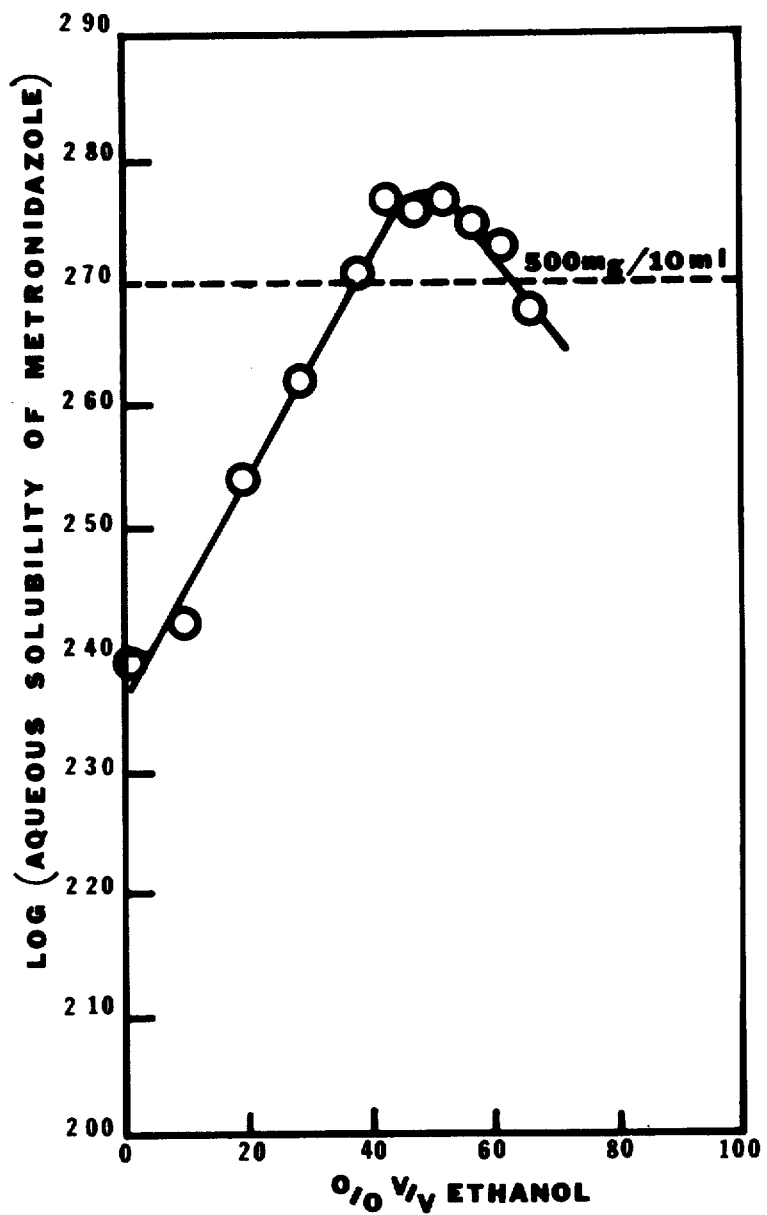
FIG. 4 is a graph illustrating the solubility of metronidazole in various mixtures of water and ethanol with a constant composition of 20% v/v N,N-dimethylacetamide and 10% v/v propylene glycol.
Figure 5:
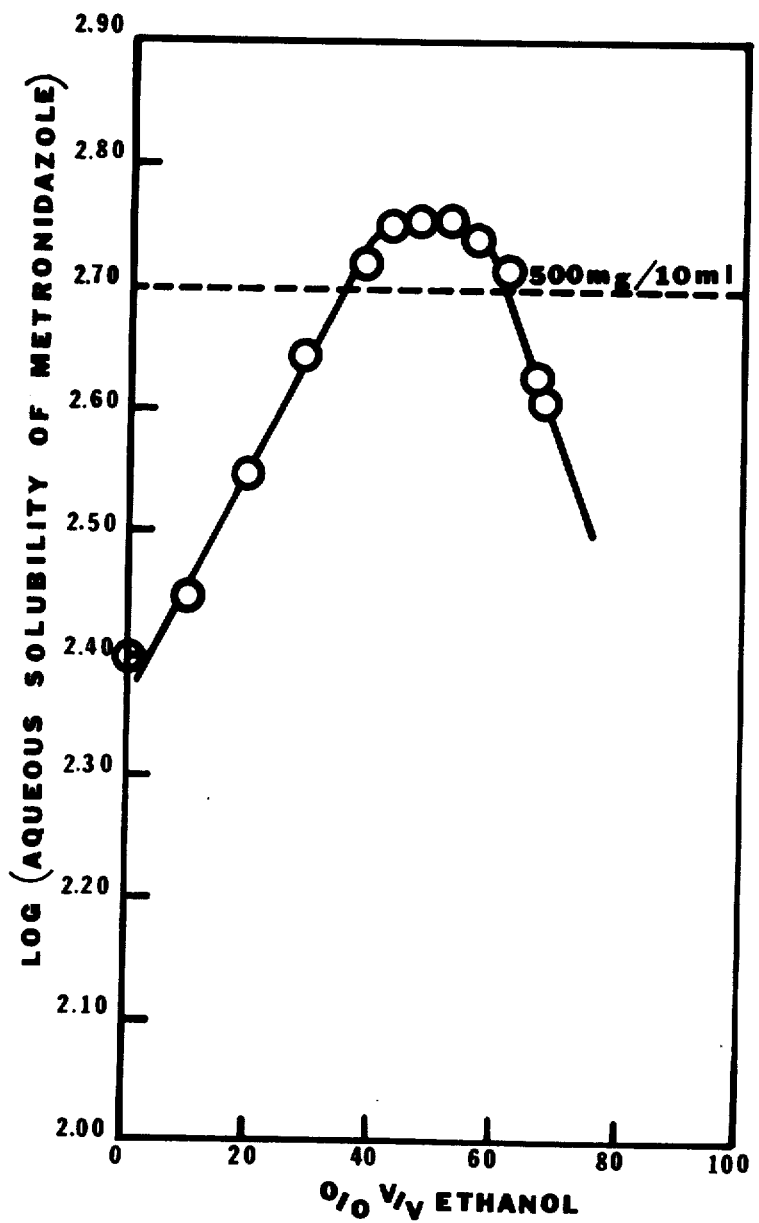
FIG. 5 is a graph illustrating the solubility of metronidazole in various mixtures of water and ethanol with a constant composition of 20% v/v N,N-dimethylacetamide and 10% v/v 2,2-dimethyl-1,3-dioxolane-4-methanol.
Figure 6:
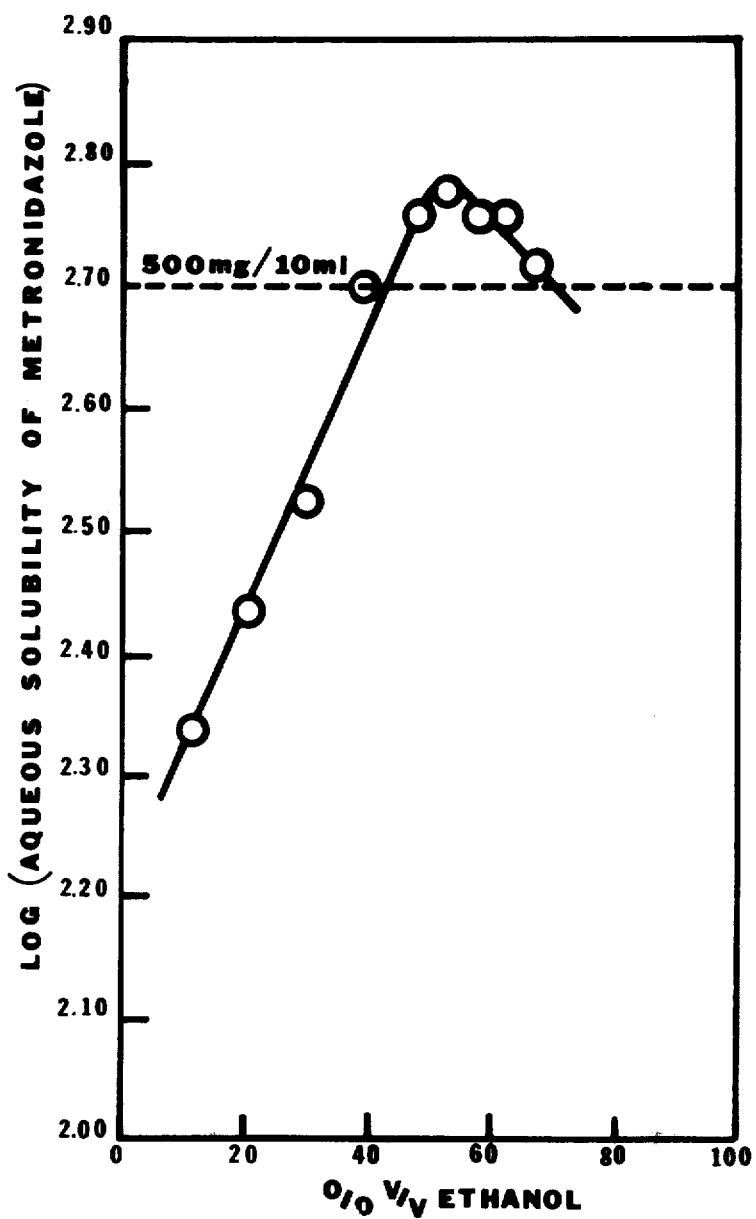
FIG. 6 is a graph illustrating the solubility of metronidazole in various mixtures of water and ethanol with a constant composition of 20% v/v N,N-dimethylacetamide and 2% w/v nicotinamide.

Also, unexpectedly, FIGS. 4, 5 and 6 illustrate that the combination of ethanol, water and N,N-dimethylacetamide can be made to dissolve more than 500 mg. of metronidazole by the addition of nicotinamide, propylene glycol or 2,2-dimethyl-1,3-dioxolane-4-methanol. These systems have the advantages of an even lower percentage composition of N,N-dimethylacetamide. Optimum systems and the solubility of metroinidazole therein are illustrated in Table 1.

TABLE 1

| Solvent System | Solubility (mg./10 ml.) |
| --- | --- |
| 30% v/v N,N-dimethylacetamide 52.3% v/v ethanol 17.7% v/v aqueous buffer | 642.2 |
| 20% v/v N,N-dimethylacetamide 52.3% v/v ethanol 25.7% v/v aqueous buffer 2% w/v nicotinamide | 631.0 |
| 20% v/v N,N-dimethylacetamide 49% v/v ethanol 21% v/v aqueous buffer 10% v/v propylene glycol | 595.7 |
| 20% v/v N,N-dimethylacetamide 47.5% v/v ethanol 22.5% v/v aqueous buffer 10% v/v 2,2-dimethyl-1,3-dioxolane-4-methanol | 575.4 |

Thus, critical solubility ranges for metronidazole which provide for a pharmaceutically acceptable and injectable unit dose form of this antimicrobial agent are provided by the present invention.

The following examples describe in detail compositions illustrative of the present invention and methods which have been devised for their preparation. It will be apparent to those skilled in the art that modifications, both of materials and methods, may be practiced without departing from the purpose and intent of this disclosure. Throughout the examples hereinafter set forth, relative amounts are given in percent by volume, except as otherwise noted. The term "q.s." refers to "quantum sufficit".

EXAMPLE 1

A solution of 2.0 parts of N,N-dimethylacetamide and 5.23 parts of ethanol are mixed together with 2.0 parts of Tris buffer at room temperature with agitation or stirring. Dissolve nicotinamide (200 mg. per 10 ml. of the final solution) into such solution with agitation. After the solution has cleared, metronidazole (500 mg. per 10 ml. of the final solution) is added and dissolved with continuous stirring, and buffer is added q.s. to 10 parts by volume. The resulting solution is stirred for 1 hour, filtered, filled into ampules, sealed and sterilized. The resulting formulation has the following composition:

| | |
| --- | --- |
| metronidazole | 500 mg. |
| N,N-dimethylacetamide | 2.0 ml. |
| ethanol | 5.23 ml. |
| nicotinamide | 200 mg. |
| Tris buffer q.s. to make | 10 ml. |
| pH of the final solution is 5.0 – 6.0 | |

EXAMPLE 2

When the procedure of Example 1 is repeated using only the appropriate amounts of metronidazole, N,N-dimethylacetamide, ethanol and Tris buffer, there is obtained a formulation having the following composition:

| | |
| --- | --- |
| metronidazole | 500 mg. |
| N,N-dimethylacetamide | 3.0 ml. |
| ethanol | 5.23 ml. |
| Tris buffer q.s. to make | 10 ml. |
| pH of the final solution is 5.0 – 6.0 | |

EXAMPLE 3

When the procedure of Example 1 is repeated using propylene glycol or 2,2-dimethyl-1,3-dioxolane-4-methanol, respectively, in place of the nicotanamide, there are obtained formulations of the following compositions:

| | |
|---|---|
| metronidazole | 500 mg. |
| N,N-dimethylacetamide | 2.0 ml. |
| ethanol | 4.9 ml. |
| propylene glycol | 1.0 ml. |
| Tris buffer q.s. | 10 ml. |
| metronidazole | 500 mg. |
| N,N-dimethylacetamide | 2.0 ml. |
| ethanol | 4.75 ml. |
| 2,2-dimethyl-1,3-dioxolane-4-methanol | 1.0 ml. |
| Tris buffer q.s. | 10 ml. |

What is claimed is:

1. An injectable metronidazole composition having 500–650 mg./10 ml. metronidazole in a solvent system comprising:
   25–35% v/v N,N-dimethylacetamide
   40–60% v/v ethanol
   10–30% v/v aqueous buffer
or
   15–25% v/v N,N-dimethylacetamide
   40–60% v/v ethanol
   10–30% v/v aqueous buffer
and including one of the following:
   1–5% w/v nicotinamide
   5–15% v/v propylene glycol
   5–15% v/v 2,2-dimethyl-1,3-dioxolane-4-methanol
said aqueous buffer maintaining the pH of the injectable metronidazole composition at 5.0–7.5.

2. A composition according to claim 1 which comprises 500–650 mg./10 ml. metronidazole in a solvent system comprising:
   15–25% v/v N,N-dimethylacetamide
   40–60% v/v ethanol
   10–30% v/v aqueous buffer
   1–5% w/v nicotinamide
said aqueous buffer maintaining the pH of the composition at 5.0–7.5.

3. A composition according to claim 1 which comprises 500–650 mg./10 ml. metronidazole in a solvent system by volume comprising:
   15–25% N,N-dimethylacetamide
   40–60% ethanol
   10–30% aqueous buffer
   5–15% propylene glycol
said aqueous buffer maintaining the pH of the composition at 5.0–7.5.

4. A composition according to claim 1 which comprises 500–650 mg./10 ml. metronidazole in a solvent system by volume comprising:
   15–25% N,N-dimethylacetamide
   40–60% ethanol
   10–30% aqueous buffer
   5–15% 2,2-dimethyl-1,3-dioxolane-4-methanol
said aqueous buffer maintaining the pH of the composition at 5.0–7.5.

* * * * *